United States Patent
Peng et al.

(10) Patent No.: US 10,792,263 B2
(45) Date of Patent: Oct. 6, 2020

(54) METHOD OF TREATING AN INDIVIDUAL HAVING A MICROBIAL INFECTION

(71) Applicant: Sun Yat-sen University, Guangzhou, Guangdong (CN)

(72) Inventors: Xuanxian Peng, Guangdong (CN); Hui Li, Guangdong (CN); Zhixue Cheng, Guangdong (CN); Chang Guo, Guangdong (CN)

(73) Assignee: Sun Yat-Sen University, Guangdong (CN)

( * ) Notice: Subject to any disclaimer, the term of this patent is extended or adjusted under 35 U.S.C. 154(b) by 0 days.

(21) Appl. No.: 14/758,301

(22) PCT Filed: Jan. 14, 2013

(86) PCT No.: PCT/CN2013/070429
§ 371 (c)(1),
(2) Date: Jun. 29, 2015

(87) PCT Pub. No.: WO2014/101322
PCT Pub. Date: Jul. 3, 2014

(65) Prior Publication Data
US 2015/0359770 A1   Dec. 17, 2015

(30) Foreign Application Priority Data
Dec. 31, 2012 (CN) .......................... 2012 1 0589250

(51) Int. Cl.
*A61K 31/198* (2006.01)
*A61K 35/14* (2015.01)
*A61K 35/16* (2015.01)

(52) U.S. Cl.
CPC ............ *A61K 31/198* (2013.01); *A61K 35/14* (2013.01); *A61K 35/16* (2013.01); *Y02A 50/30* (2018.01)

(58) Field of Classification Search
CPC ................................................. A61K 31/198
See application file for complete search history.

(56) References Cited

U.S. PATENT DOCUMENTS 3,674,863 A * 7/1972 Fisher .................. A61K 39/104
424/170.1
7,999,007 B2   8/2011 Jeffs 2009/0280102 A1* 11/2009 Becquerelle ............ A61K 38/44
424/94.4
2010/0297081 A1* 11/2010 Huang ................. A61K 9/0019
424/85.7
2013/0071439 A1   3/2013 Losick

FOREIGN PATENT DOCUMENTS

| CN | 101647808 A | * | 2/2010 |
| CN | 101827612 A | | 9/2010 |
| CN | 102791262 A | | 11/2012 |
| WO | WO-2010142017 A1 | * | 12/2010 ........... A61K 38/212 |

OTHER PUBLICATIONS

Alexander et al. "Bactericidal Activity of Human Serum Against *Escherichia coli* X1776". Infection and Immunity, p. 837-841 (Year: 1980).*
Li et al. Hindawi Case Reports in Infectious Diseases. vol. 2019, Article ID 2094372, 3 pages (Year: 2019).*
Ho et al. Vibrio Infections from Medscape. Updated: Jul. 24, 2018. Retrieved from the Internet on Jan. 3, 2020. Retrieved from: <URL: https://emedicine.medscape.com/article/232038-medication>. (Year: 2018).*
Reed et al. "Treatment of beta-hemolytic streptococcal pharyngitis with cefaclor or penicillin. Efficacy and interaction with beta-lactamase-producing organisms in the pharynx." J Fam Pract. Feb. 1991;32(2):138-44. abstract only. (Year: 1991).*
Journal of Henan University of Science and Technology: Natural Science vol. 27, No. 5, Oct. 2006, 6 pages (English abstract included).
Hong et al., "Lysophosphatidylcholine Increases Neutrophil Bactericidal Activity by Enhancement of Azurophil Granule-Phagosome Fusion via Glycine-GlyR α2/TRPM2/p38 MAPK Signaling" The Journal of Immunology, Mar. 2010, 15 pages.
"Lack of bactericidal activity against *E. coli* in serum of hepatic cirrhosis patients", Foreign Medical Information, No. 4, 1980, 1 page (cited in International Search Report; Chinese language only).
Liu et al., "Changes in Phospholipase A2 in Blood of Rat Bacterial Infection Model" Chinese Journal of Nosocomiology vol. 13, No. 1, 2003, 3 pages (English abstract included).
International Search Report issued in International Application No. PCT/CN2013/070429 dated Oct. 17, 2013, 6 pages.

* cited by examiner

*Primary Examiner* — Amy L Clark
(74) *Attorney, Agent, or Firm* — Cooper Legal Group, LLC

(57) ABSTRACT

Glycine, threonine, and serine can enhance the sensitivity of bacteria to serum, plasma, or whole blood, and therefore can be used as molecules to improve the bactericidal effect of the serum, the plasma, or the whole blood.

8 Claims, 6 Drawing Sheets

METHOD OF TREATING AN INDIVIDUAL HAVING A MICROBIAL INFECTION

FIELD OF THE INVENTION

This invention provided herein belongs to the field of medical and pharmaceutical technology, which relates generally to a small molecule capable of enhancing bacteria's susceptibility to serum.

BACKGROUND OF THE INVENTION

After bacteria enter the body, the body clears away the bacteria via innate and acquired immunity. Acquired immunity mainly functions through antibodies in the blood, whereas innate immunity targets the bacteria primarily through complement system and phagocytic cells.

Bacterial lysis by the complement system is one of the major ways that organisms use to clear bacteria that enter the blood and stick to the mucosal membrane. This effect can be dependent or independent of antibodies. Complement system is a group of proteins present in the serum and tissue fluid of human and other vertebrates with enzymatic activities upon activation. This group of proteins comprises more than 30 soluble and membrane-bound proteins. Complement system is an important immune effector system as well as an immune response amplification system with critical biological role in vivo, which participates extensively in defense responses to microbes and immunomodulation in the organism. This system also mediates immunopathological damage response.

However, a variety of bacterial pathogens confer noticeable serum resistance, which can prevent complement lysis and is one of the important pathogenic features of pathogens. Research in the past century has indicated that bacterial resistance to serum complement lysis is mainly mediated through lipopolysaccharide (LPS) and membrane (outer membrane) proteins. Bacteria can reduce the binding of membrane (outer membrane) proteins with complement and inactivate the complement already bound to membrane (outer membrane) proteins, which enables bacterial resistance to serum. Therefore, elimination of serum resistance is an important means of prevention and treatment of infections by bacterial pathogens. However, there is currently no research yet reporting a method that aims to increase serum bactericidal effect by inhibiting serum resistance. Thus, the discovery of new compounds that can increase bacterial lysis by the complement system will be significant and beneficial to prevent and treat bacterial infections and protect public health.

SUMMARY OF THE INVENTION

The invention aims to provide a use of a small molecule that can enhance serum susceptibility of bacteria. As a small metabolite that promotes bacteria's serum susceptibility, this invention can thereby effectively inhibit bacterial pathogens by these small molecules.

The small molecules mentioned in this invention belong to amino acids or their derivatives.

More specifically, the amino acids herein could be glycine, threonine or serine.

Preferably, the amino acid is glycine (Gly).

Thus, the invention discloses and protects the use of amino acid(s) or its/their derivative(s) in the manufacture of pharmaceuticals that can increase bactericidal effect of serum, plasma or whole blood, wherein the amino acid is glycine, serine or threonine.

Meanwhile, the invention discloses and protects the use of the amino acid(s) or its/their derivative(s) in the preparation of injectable bactericide.

Also, the invention discloses and protects the use of amino acid(s) or its/their derivative(s) used in conjunction with serum, plasma or whole blood in the preparation of bactericidal medicaments, wherein the amino acid refer to glycine, threonine or serine.

Preferably, the amino acid is glycine.

Metabolites of glycine and glycine derivatives include glutathione, 5,10-methylenetetrahydrofolate, H-Protein-S-aminomethyldihydrolipoyllysine, N1-(5-Phospho-D-ribosyl)glycinamide, L-2-Amino-3-oxobutanoate, and L-cysteine.

In addition, this invention protects a bactericidal pharmaceutical composition, wherein the composition comprises amino acid(s) and in the meanwhile serum/plasma/whole blood, wherein the amino acid is glycine, threonine or serine.

Preferably, the ratio of glycine to serum is 1:3000 (weight/weight).

Accordingly, the bacteria refer to gram-negative or gram-positive bacteria. Preferably, the bacteria are gram-negative or gram-positive bacterial pathogens. More preferably, the bacteria refer to *Staphylococcus aureus*, *Edwardsiella tarda*, beta-hemolytic *Streptococcus*, *Pseudomonas aeruginosa*, *Escherichia coli* or *Vibrio*.

Preferably, serum, plasma or whole blood is from mammals, fish or poultry.

This invention also discloses and protects a bactericidal method, which involves the use of amino acid(s) in conjunction with serum/plasma/whole blood, or the use of the amino acid derivative(s) in conjunction with serum/plasma/whole blood, wherein the amino acid is glycine, threonine or serine.

Preferably, the method aforementioned is as follows: by a weight ratio of 1:3000, glycine and serum are mixed for killing gram-negative or gram-positive bacteria; 0.1 to 24 hours is taken for killing.

More preferably, the amino acid used in this invention is glycine.

This invention employed metabolomics to analyze all small molecule metabolites of *Escherichia coli* treated with human serum and discovered that the glycine level in *Escherichia coli* decreased significantly, suggesting that it could be used as a small molecule metabolite to enhance the serum susceptibility of bacteria.

This invention investigated the serum bactericidal effect by adding glycine in three separate scenarios: a fixed amount of human serum combined with different concentrations of glycine, a fixed concentration of glycine combined with different volumes of human serum, and a fixed amount of human serum and glycine incubated for different time periods. The results showed that the control group with only glycine had no effect on the growth of *Escherichia coli*, whereas adding glycine in human serum increased the bactericidal effect. In addition an incremental effect was seen with increasing concentration of glycine and serum. Meanwhile, within a certain time range, the effect increased with prolongation of incubation time. Besides, the replacement of serum by plasma could also obtain the same effect, but serum or plasma with inactivated complement yielded no effect.

Through bactericidal experiments using various bacteria such as gram-positive bacteria including *Staphylococcus aureus* and beta-hemolytic *Streptococcus* and gram-negative bacteria including *Escherichia coli, Edwardsiella tarda, Pseudomonas aeruginosa* and *Vibrio*, the results showed that adding glycine can increase the susceptibility of all the tested bacteria to human serum.

The invention investigated the bactericidal effect of killing major pathogens with glycine added to the serum/plasma from animals of different evolutionary levels, including mice, rabbits, pigs, chickens, pigeons, shrimps and fishes. The results showed that glycine was capable of enhancing the bactericidal effect of serum from different animals to kill major pathogens.

This invention further performed in vivo experiments in mice and found that adding glycine improved significantly the scavenging capacity against not only a model *Escherichia coli* strain but also a clinically isolated pathogenic strain that is completely serum-resistant. The result indicated that the glycine could function in vivo and in whole blood.

In summary, adding glycine can significantly improve the susceptibility of bacteria to serum, which provides a new technical approach for treating infections caused by serum-resistant pathogens.

Thus, the invention discloses and protects the use of glycine in increasing bacteria susceptibility to serum. It may be used to prepare a pharmaceutical agent or bactericide that further enhances bacterial susceptibility to serum.

Meanwhile, the invention discloses and protects a method for improving bacteria's susceptibility to serum, wherein glycine is used as a pharmaceutic to enhance the bactericidal effect of serum against bacteria.

In the described examples of bacteria of the invention, non-limiting examples of bacteria include *Staphylococcus aureus*, Beta hemolytic *streptococcus*, *Edwardsiella tarda*, *Pseudomonas aeruginosa*, *Escherichia coli* and *Vibrio* spp. These bacteria, including *Staphylococcus aureus* and beta-hemolytic *streptococcus* as gram-positive bacteria, and *Escherichia coli*, *Pseudomonas aeruginosa*, *Edwardsiella tarda*, *Vibrio parahaemolyticus* and *alginolyticus* as gram-negative bacteria, are common pathogens in humans and farm animals. Especially, *Escherichia coli* is a model bacteria for investigating serum-resistance. These bacteria are common pathogens in humans and farm animals. In addition, serum-resistant strains of these bacteria are frequently isolated. Therefore, these bacteria are good representatives of serum-resistant bacteria.

When the methods above are applied to enhance bacterial susceptibility to serum, the working concentration of glycine is 0.05-1 g/kg body weight/day.

According to the present invention, a new bactericide containing glycine can be prepared. Alternatively, a bactericide with glycine as the main component for enhancing serum bactericidal effect can be prepared.

FIGURE LEGENDS

Figure 6:
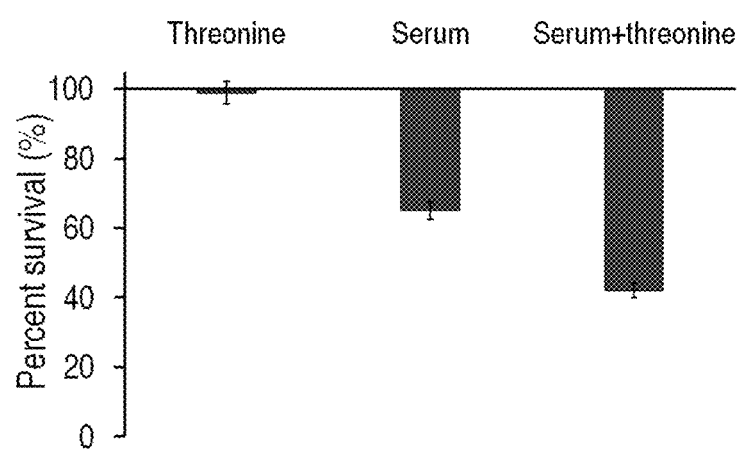

FIG. 6. Glycine improves clearance of *E. coli* from mice

DESCRIPTION OF THE EMBODIMENTS

Below with reference to specific embodiments, this invention is further illustrated. It should be understood that these embodiments are merely illustrative of the present invention and are not intended to limit the scope of the invention.

Example 1

Glycine Serves as a Biomarker of the *E. coli*'s Resistance to the Bactericidal Effect of Serum Sample preparation: Single colonies of the parent strain *E. coli* K12 BW25113 are picked from Luria-Bertani (LB) agar plate, inoculated into 5 mL LB medium and incubated with shaking at 200 rpm, 37° C. for 16 hours. Cultures are then diluted 1:100 (v/v) in 200 mL fresh LB medium and grow to an $OD_{600}$ of 1.0 at 37° C. with shaking. Cells are collected by centrifugation at 8000 rpm for 10 minutes at 4° C. and washed with 0.85% saline once.

GC-MS Sample Preparation and Data Processing

GC-MS samples are prepared as follows. Aliquots of 100 µL human serum (Blood is drawn from healthy donors and coagulates naturally. After centrifugation, supernatant is the serum) were added to bacterial cells. The cells are resuspended and cultured for 1 hour at 37° C. with shaking at 200 rpm. Saline serves as control. The cells are centrifugated for 5 minutes at 8000 rpm at 4° C. for 5 minutes to collect the bacteria and remove residual serum or saline. Cells are adjusted to an $OD_{600}$ of 1.0 with saline. 1 mL cells are mixed with cold methanol (containing 5 µL 0.1 mg/mL ribitol (Sigma) as an analytical internal standard). Cells are lysed by sonication for 3 minutes at a 10 W power setting and centrifuged for 10 minutes at 12,000 rpm at 4° C. 500 µL supernatant is transferred into a new 1.5 mL centrifuge tube and dried in a rotary vacuum centrifuge device (LAB-CONCO). The resulting samples are used for GC/MS analysis. Three biological replicates are carried out for each sample.

GC-MS analysis: Samples are firstly protected by methylation on the carbonyl moieties. Specifically, the samples go through a 90 minutes reaction at 37° C. with 40 µL pyridine containing 20 mg/mL methoxyamine hydrochloride. This is followed by derivatization of acidic protons by a 30 min reaction at 37° C. with the addition of 80 µL N-methyl-N-trimethylsilyltrifluoroacetamide (MSTFA, Sigma-Aldrich). 1 µL derivatizated sample is injected into DBS-MS column with an inner diameter of 30 m×250

μm×0.25 μm using splitless model in DSQ II (Thermo Scientific) for analysis. The initial GC oven temperature is maintained at 85° C. for 5 minutes, and then at a rate of 15° C./min of increase to 330° C., maintained for 5 minutes. 1 mL/min flow of Helium is used as a carrier gas. The MS is operated at a range of 50-600 m/z.

Data processing includes spectral deconvolution and calibration using AMDIS and the internal standard. Retention time alignment is applied to all samples for calibration. Using RT as reference, all the spectrums are searched and assembled to generate a file containing the abundance information of each metabolite of all the samples. Metabolites of GC-MS are compared and identified by searching the National Institute of Standards and Technology (NIST) database with the NIST MS search 2.0 software. The output data matrix are corrected using the total peak area. Using retention time and m/z match results to give each substance in each sample a standardized peak intensity, the files are then used for further statistical analysis.

3. Data Analysis

Figure 1A:
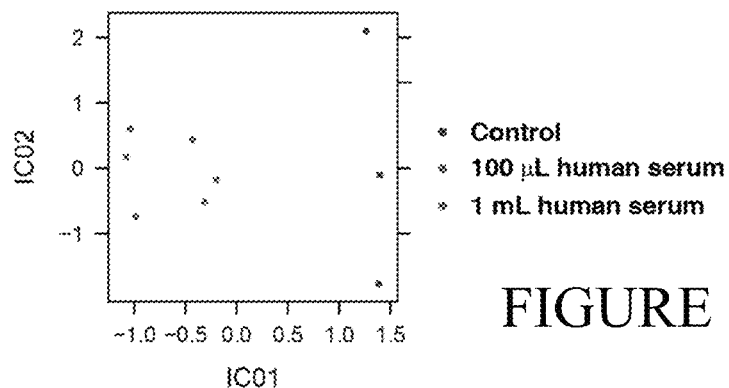
FIG. 1A shows the results of an independent component analysis of serum-resistant *E. coli* by GC-MS.
Figure 1B:
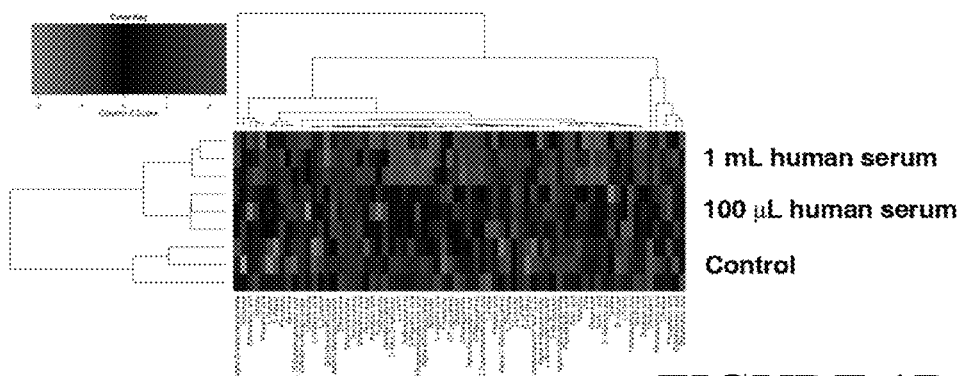
FIG. 1B shows the results of an independent component analysis of serum-resistant *E. coli* by cluster analysis.
Figure 1C:
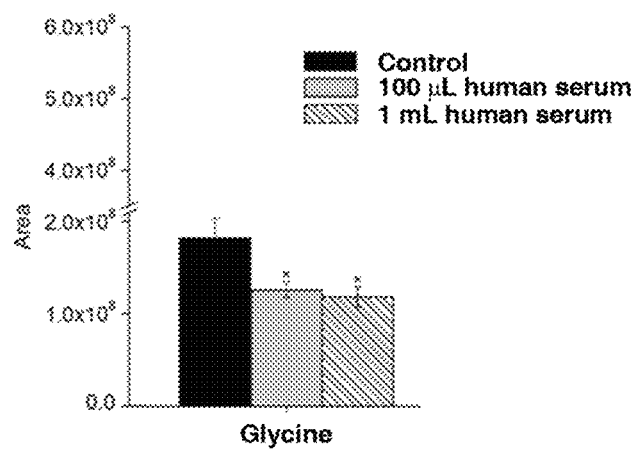
FIG. 1C shows the results of an independent component analysis of serum-resistant *E. coli* by metabolite content analysis.

Metabolites of *E. coli* treated by saline control or 100 μL human serum are identified by GC-MS. Heat map and hierarchical clustering analysis show that three replicates of each sample are clustered together and human serum treated groups are clustered together (FIG. 1A). Independent component analysis shows that IC01 explains well the effect of human serum (FIG. 1B). Glycine decreases significantly in human serum treated samples according to the statistical analysis of all the metabolites (FIG. 1C). This suggests that glycine is a biomarker, which may be a molecule that *E. coli* targets to resist bactericidal action by serum.

Example 2

Glycine can Increase *E. coli*'s Susceptibility to Serum

To understand whether glycine enhances the bactericidal effect of serum, experiments are carried out in 3 scenarios: the same volume of human serum mixed with different concentrations of glycine, different volumes of human serum mixed with the same concentration of glycine, and these mixtures are treated for different incubation periods.

Figure 2A:
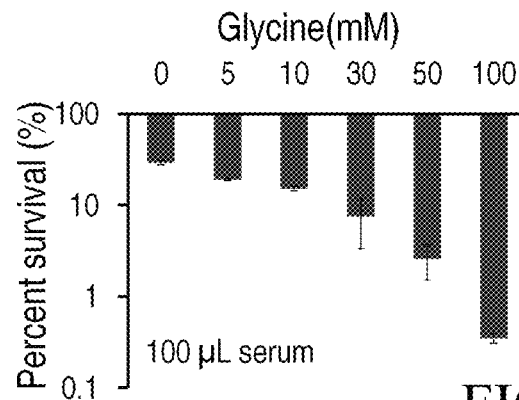
FIG. 2A shows how glycine increases *E. coli*'s susceptibility to serum for different concentrations of glycine.

1. Glycine Elevates Bacterial Susceptibility to Serum Killing in a Glycine Dose-Dependent Manner Bacterial cells are prepared according to Example 1.1. Glycine is added to a final concentration of 0, 5, 10, 30, 50 and 100 mM and the mixtures are cultured for 1 hour at 37° C. with shaking at 200 rpm. Then 100 μL of human serum or saline are added as test and control groups, respectively. Bacteria are cultured for 2 hours and collected by centrifugation. Cells are resuspended with 1 mL of saline. Live bacterial cells are counted on LB agar plate. Survival rate is calculated as follows: number of live bacteria cells after treatment with different concentrations of glycine supplementation/number of live bacteria cells after treatment with saline×100%. In FIG. 2A, we show the survival rate of *E. coli* in the presence of human serum with different concentrations of glycine. These results show that 5 mM glycine increases the serum bactericidal effect by 1.36-fold, and the serum bactericidal effect gradually increases with increasing concentration of glycine, in which the highest effect, approximately an 86-fold elevation, is detected in 100 mM glycine supplementation.

Figure 2B:
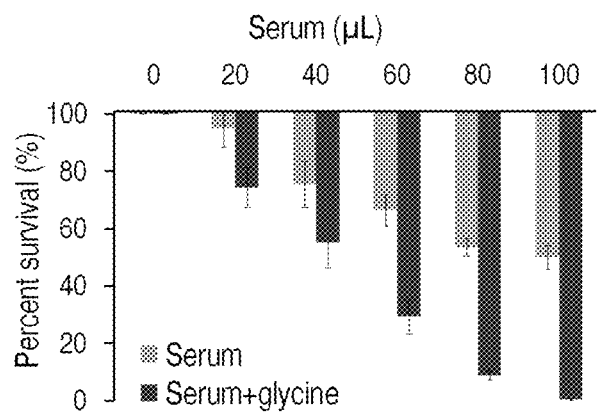
FIG. 2B shows how glycine increases *E. coli*'s susceptibility to serum for different volumes of serum.

2. The Effect of Glycine in Elevating the Serum Bacteriacidal Effect Increases with Increasing Volume of Serum Bacterial samples are prepared and added with 100 mM glycine and cultured for 1 hour at 37° C. with shaking at 200 rpm. Then 0, 20, 40, 60, 80 or 100 μL human serum is added and cultured for 2 hours at 37° C. with shaking at 200 rpm. The controls are not mixed with glycine but only with different volumes of human serum. Bacteria are collected by centrifugation and resuspended with 1 mL of saline for spot-plate counting. The survival rate is calculated as follows: the number of live bacteria cells after treatment with glycine plus different volumes of human serum/the number of live cells after treatment with only human serum×100%. Cell counting results (FIG. 2B) show that the presence of glycine improves serum bactericidal effect against *E. coli* as compared to the absence of glycine. The bactericidal effect increases with increasing amount of serum, in which 86-fold elevation is detected with 100 μL human serum.

Glycine Promotes Serum Bactericidal Effect in a Time-Dependent Fashion

Figure 2C:
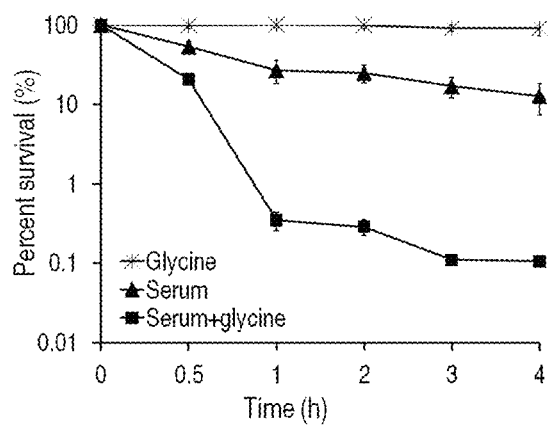
FIG. 2C shows how glycine increases *E. coli*'s susceptibility to serum over different incubation periods.

The prepared bacterial samples are divided into 4 groups and treated separately as follows: with 100 mM glycine, 100 μL human serum, 100 μL human serum plus 100 mM glycine or saline alone as control. The mixtures are cultured for 0.5, 1, 2, 3, and 4 hours at 37° C. with shaking at 200 rpm. Bacteria are collected by centrifugation and resuspended in 1 mL saline. Bacteria are counted using LB agar plates. The survival rate is calculated as follows: the number of live bacteria after treatment with serum and/or glycine in different times/the number of live bacteria in the saline control group×100%. FIG. 2C shows the survival rates of 3 test groups in different times. The figure suggests that there is no bactericidal effect with glycine addition alone. Bactericidal effect is detected in the groups containing serum. Higher bactericidal effect is significantly improved in the groups with serum plus glycine, with 2-fold increase after 0.5 hours, 77-fold after 1 hour and 120-fold after 4 hours.

In conclusion, glycine itself has no influence on the growth of *E. coli* and serum has a certain bactericidal effect. However, synergy of serum with glycine increases bacterial susceptibility to serum killing in glycine and serum dose-dependent manners.

Example 3

Figure 3A:
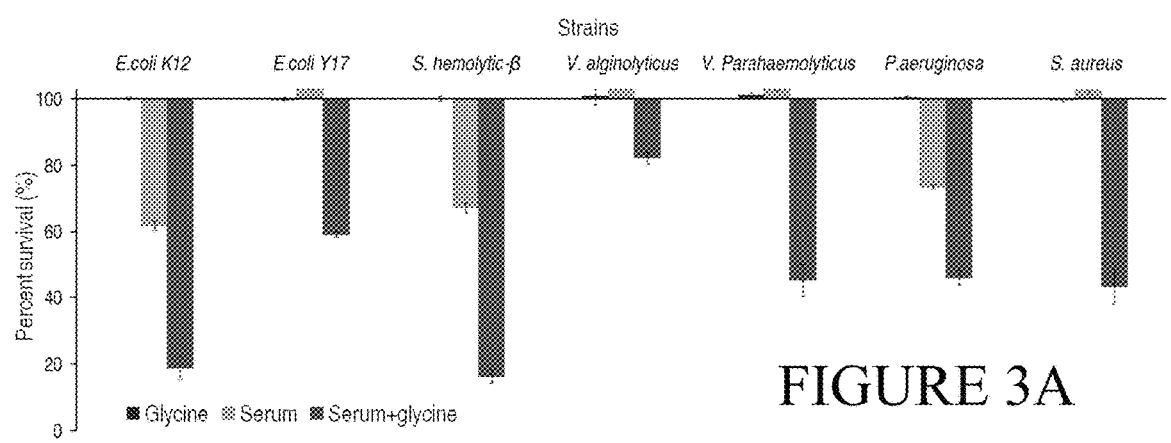
FIG. 3A shows how glycine increases serum susceptibility of various bacteria in terms of survival rate.
Figure 3B:
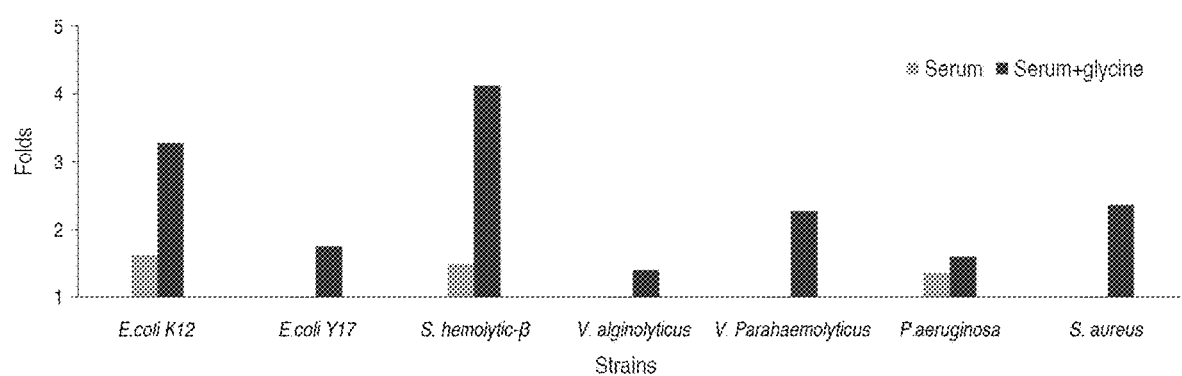
FIG. 3B shows how glycine increases serum susceptibility of various bacteria in terms of fold increased.

Glycine Improves Gram-Negative and Gram-Positive Bacteria's Susceptibility to Serum A variety of bacteria (*E. coli* K12 BW25113, *E. coli* clinical strain Y17, beta-hemolytic *Streptococcus*, *Vibro alginolyticus*, *Vibro parahaemolyticus*, *Pseudomonas aeruginosa* and *Staphylococcus aureus*) are cultured as described in Example 1.1. Aliquots of 3 mL cells of each bacterium with $OD_{600}$ of 1.0 are collected and divided into 4 groups respectively. These groups are added with 100 μL saline as control, 100-150 mM glycine, 125-175 μL human serum or 125-175 μL human serum plus 100-150 mM glycine, respectively. Optimal bactericidal effect is slightly different with various amounts of serum plus glycine for different types of bacteria. Bacteria cells are cultured at 37° C. with shaking at 200 rpm and harvested by centrifugation after 4 hours. Bacteria are resuspended with 1 mL of saline and measured at OD 600 nm of absorbance. The OD of the three treatments and comparison of killing ratios between serum and serum plus glycine are shown in FIG. 3A and FIG. 3B, respectively. As seen in the Figure, serum bactericidal effect against different bacteria types is not the same. Serum has a certain bactericidal effect on *E. coli* K12 BW25113, beta-hemolytic *Streptococcus* and *P. aeruginosa*, while it promotes the growth of other bacteria. However, significant bactericidal effect is detected in all the samples when glycine is added, which increases the effect by more than 1-fold and up to 4.13-folds.

Example 4

Figure 4A:
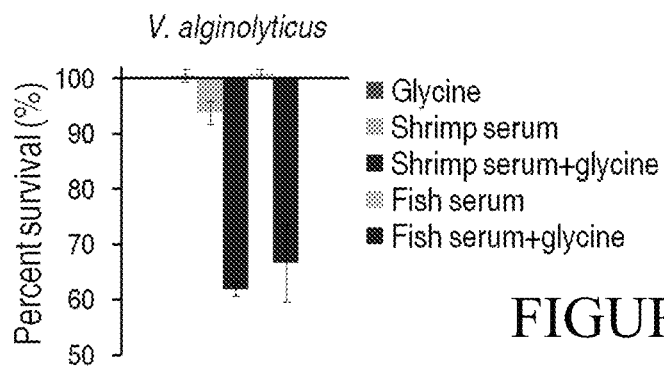
FIG. 4A shows how glycine increases the bactericidal effects of shrimp and fish serum against *V. alginolyticus*.
Figure 4B:
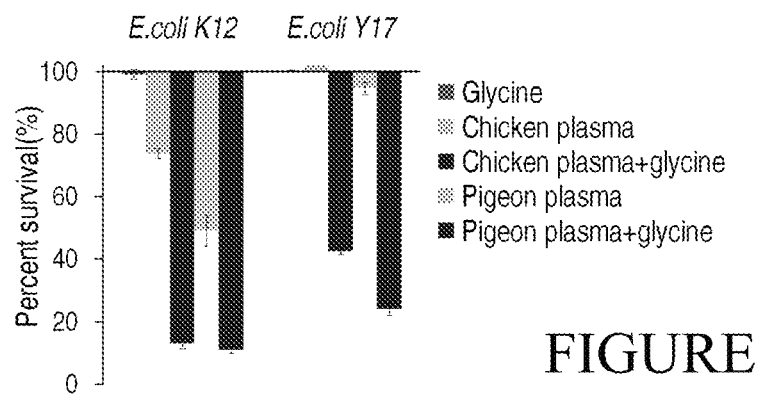
FIG. 4B shows how glycine increases the bactericidal effect of chicken and pigeon serum against *E. coli*.
Figure 4C:
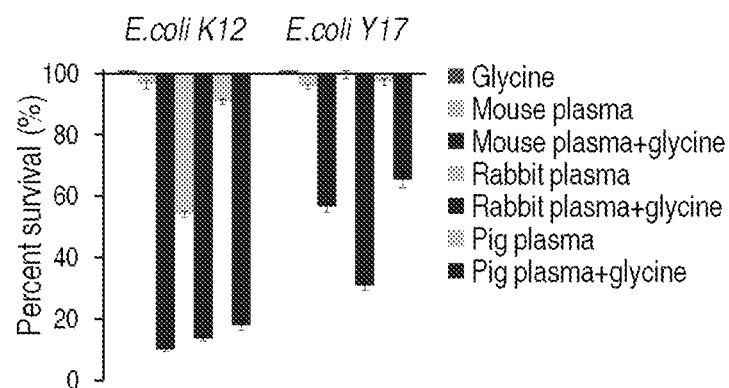
FIG. 4C shows how glycine increases the bactericidal effect of mouse, rabbit and pig plasma against *E. coli*.

Glycine Improves Bactericidal Effect of Serum from Different Evolutionary Levels of Animals Against Major Bacterial Pathogens A variety of bacteria (*E. coli* K12 BW25113, *E. coli* clinical strain Y17, Vibro *alginolyticus*, Vibro *parahaemolyticus*, *Pseudomonas aeruginosa* and *Staphylococcus aureus*) are cultured as described in Example 1.1. Aliquots of 3 mL bacteria are collected with $OD_{600}$ of 1.0. Then, 100 μL serum/plasma from different animals or 100 μL serum/plasma of different animals plus 100 mM glycine are added and 100 mM glycine alone is used a control. Cells are cultured for 4 hour at 37° C. with shaking at 200 rpm. Bacteria are resuspended with 1 mL of saline. Absorbance is measured at 600 nm. FIG. 4 shows the OD of the samples treated by serum/plasma from different evolutionary levels of animals with and without glycine. As seen in the Figure, serum/plasma from different evolutionary levels of animals have certain bactericidal effect on their major bacterial pathogens and the effect is significantly elevated in the presence of glycine, with an increase of minimum 1.5-fold and a maximum of ~10-folds. These results suggest that glycine can significantly improve susceptibility of major bacterial pathogens to serum/plasma from different evolutionary levels of animals.

Example 5

Glycine Increases Mouse's Ability in Scavenging *E. coli*

Figure 5A:
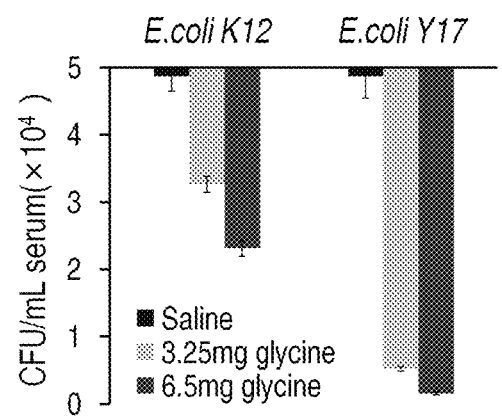
FIGS. 5A and 5B represent, respectively, the effect of glycine to clear bacterial pathogens in vivo in mice in terms of the number of bacteria and the bacteria survival rate in the blood of mice with or without glycine injection.
Figure 5B:
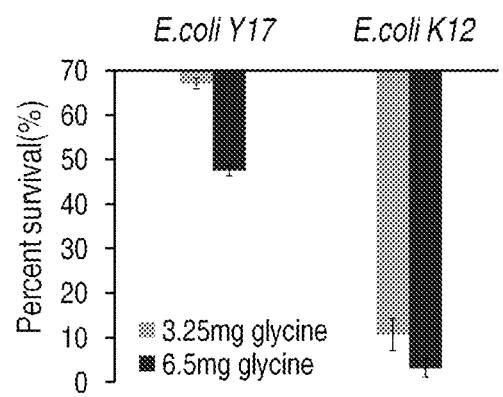

A total of 15 6-week-old mice (purchased from the Laboratory Animals Center of Sun Yat-sen University) are randomly divided into three groups: saline control group and two treatment groups are administered with 3.25 or 6.5 mg glycine/mouse. The compound is intravenously administered at 3.25 or 6.5 mg glycine/injection/mouse every 12 hours and 6 times in total. Mice are intravenously injected $1 \times 10^6$ *E. coli* K12 BW25113 or *E. coli* clinical isolate Y17 at 12 hours after the last administration of glycine. Blood is withdrawn from mouse tail vein at 48 hours. The clearance of bacteria is determined by plate counting. In vivo bacterial number and survival rate for treatment groups with 2 different glycine concentrations are shown in FIGS. 5A and B, respectively. The results show that the bacterial number is reduced significantly in mice when they are injected with glycine. Clearance rates of *E. coli* K12 BW25113 are 89.32% and 96.85% with injection of 3.25 mg and 6.5 mg glycine, respectively. Clearance rates of *E. coli* clinical isolate Y17 are 32.95% and 52.53% with administration of 3.25 mg and 6.5 mg glycine, respectively. These results suggest that glycine enhances bacterial clearance by serum and the serum scavenging activity against bacteria elevates with increasing dose of glycine.

Example 6

Threonine can Increase *E. coli*'s Susceptibility to Serum

The prepared bacterial cells are divided to four groups. They are added with 100 mM threonine, 100 μL human serum, 100 μL human serum plus 100 mM threonine or saline as control, respectively, and cultured at 37° C. with shaking at 200 rpm for 2 hours. The bacteria are collected by centrifugation and resuspended with 1 mL of saline. Absorbance is measured at 600 nm Survival rate is calculated as follows: the OD in groups after treatment with serum, threonine or serum plus threonine/the OD in the control group treated with saline×100%. FIG. 6 shows the survival rate of three experimental groups at different times. As shown in the Figure, no bactericidal effect is detected in the group with threonine alone. Certain bactericidal effect is detected in the group with serum alone. Compared with the group with serum alone, the group with serum plus threonine has a significant 1.5-fold increase of bactericidal effect.

What is claimed is:

1. A method of treating an individual having a microbial infection, the method comprising:
administering to the individual having a microbial infection an effective amount of a pharmaceutical formulation comprising glycine or a glycine derivative, and, optionally, one or more of serine and threonine, wherein the glycine or glycine derivative, and optionally, one or more of serine or threonine, wherein the glycine or glycine derivative is present, and the serine and threonine, respectively, when present, is present in an effective amount to elevate a bactericidal effect of a biological fluid comprising serum, plasma or blood against the microbial infection, and to kill a gram-negative bacterial pathogen or gram-positive bacterial pathogen within the biological fluid, and wherein the microbial infection is induced by the gram-negative bacterial pathogen or the gram-positive bacterial pathogen selected from *Edwardsiella tarda*, beta-hemolytic *Streptococcus*, *Escherichia coli* and *Vibrio*.

2. The method of claim 1, wherein administering the effective amount of the pharmaceutical formulation comprises injecting the individual with the pharmaceutical formulation.

3. The method according to claim 1, wherein the biological fluid comprises serum, and the serum and the glycine or a glycine derivative, and, optionally, one or more of serine or threonine are mixed in a weight ratio of 1:1-3000 respectively, to kill the gram-negative bacterial pathogen or the gram-positive bacterial pathogen within a period from 0.1 hours to 24 hours from introduction of the one or more amino acid compounds to the serum.

4. The method according to claim 1, wherein the serum, plasma, or blood is from mammals, fish, or poultry.

5. The method according to claim 2, wherein the biological fluid comprises serum, and the serum and the glycine or a glycine derivative, and, optionally, one or more of serine or threonine are mixed in a weight ratio of 1:1-3000 respectively, to kill the gram-negative bacterial pathogen or the gram-positive bacterial pathogen within a period from 0.1 hours to 24 hours from introduction of the one or more amino acid compounds to the serum.

6. The method of claim 1, wherein the microbial infection is induced by the gram-negative bacterial pathogen *Edwardsiella tarda*.

7. The method of claim 1, wherein the microbial infection is induced by the gram-positive bacterial pathogen beta-hemolytic *Streptococcus*.

8. The method of claim 1, wherein the microbial infection is induced by the gram-negative bacterial pathogen *Vibrio*.

* * * * *